(12) United States Patent
Melrose

(10) Patent No.: US 6,272,468 B1
(45) Date of Patent: Aug. 7, 2001

(54) CLINICAL, HEORISTIC, ADMINSTRATIVE, RESEARCH & TEACHING (CHART) JAVA-WEB-OBJECT INFORMATION SYSTEM FOR MEDICAL RECORD MANAGEMENT PREDICATED ON HUMAN BODY ANATOMY AND PHYSIOLOGY MULTI-MEDIA MODELING

(76) Inventor: John Peter Melrose, 108 Lee Dr., Annapolis, MD (US) 21403

( * ) Notice: Subject to any disclaimer, the term of this patent is extended or adjusted under 35 U.S.C. 154(b) by 0 days.

(21) Appl. No.: 08/982,026

(22) Filed: Dec. 1, 1997

(51) Int. Cl.$^7$ ..................................................... G06F 17/60
(52) U.S. Cl. ................................................ 705/2; 707/104
(58) Field of Search .............................. 705/2, 3; 707/1, 707/10, 104, 500, 501, 513

(56) References Cited

U.S. PATENT DOCUMENTS

| | | | |
|---|---|---|---|
| 5,666,953 | * | 9/1997 | Wilk ..................................... 600/407 |
| 5,715,823 | * | 2/1998 | Wood et al. .......................... 600/437 |
| 5,793,933 | * | 8/1998 | Iwamasa ................................. 706/45 |
| 5,805,796 | * | 9/1998 | Finch et al. ............................ 714/40 |
| 5,890,129 | * | 3/1999 | Sprungeon ................................ 705/4 |
| 5,903,889 | * | 5/1999 | De La Huerga et al. ................ 707/3 |
| 5,935,060 | * | 8/1999 | Iliff ...................................... 600/300 |
| 5,960,085 | * | 9/1999 | de la Huerga ........................ 713/182 |
| 6,029,169 | * | 2/2000 | Jenkins ................................. 707/100 |

FOREIGN PATENT DOCUMENTS 58-102534 * 6/1983 (JP) ....................................... 438/17

OTHER PUBLICATIONS

"Data Configurable Diagnostic Controller"; IBM Technical Disclosure Bulletin; Jun. 1, 1994, vol. 37, No. 6A, pp. 107–112.*

Navathe: "Evolution of Data Modeling for Databases"; Communications of the ACM, Sep. 1992, v35, n9, pp. 112–123.*

* cited by examiner

Primary Examiner—Edward R. Cosimano

(57) ABSTRACT

An Internet-based computer system for determining, demonstrating and documenting human body physiology at all morphological levels and anatomic sites. The system implements Web-object, multi-media and database technologies to model and record the variable human body biochemical equilibrium and its physiological and anatomical manifestations at the genome, cell, tissue, organ and system levels; and the effects of changes in equilibrium caused by the introduction of foreign chemical substances via specific anatomic "sites" or "routes of administration". An authorized clinician user can: access the system via a secure Web page; make a virtual copy of the system model for a particular patient, research subject or other actual or hypothetical case; make virtual copies of the case model at medically significant points in time and/or at the discretion of the clinician; depict the introduction of substance(s) of specific composition, quantity and concentration via specific human body site(s) by recording data using input interface (s) representative of the site(s); inspect the model via anatomic site-specific output interface(s) that demonstrate the effect(s) of foreign substance(s) in terms of biochemical behaviors and states, and anatomical and physiological structure and function; and document the chemical introductions and effects by recording resulting behaviors and states of the case model automatically, with or without manually recorded supplementary information, per a typical healthcare industry medical record organization and format. The patient can access copies of the patient's own model(s) and accompanying medical record via a secure Web page. Both user types can email model and record instance(s) with encryption at will.

2 Claims, 4 Drawing Sheets

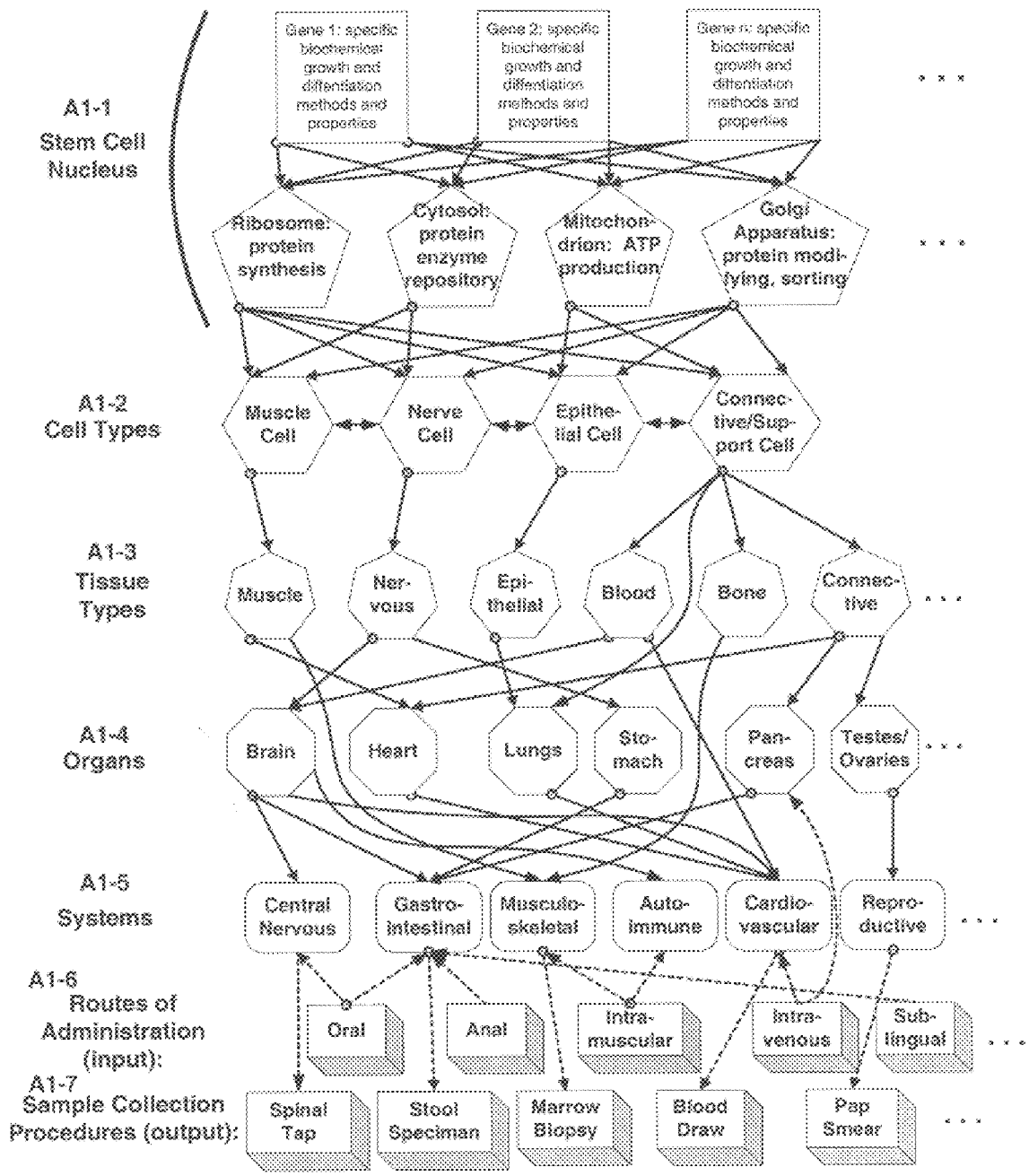

Figure A2

ChartSystem Package, medicalRecord Abstract Class

*N.B.* – Classes and methods are modified as/if needed to maintain compliance with current revision of the "IM – Information Management Standard" and its relevant subparts, as noted below, of the "hospital Accreditation Standards" of the Joint Commission for the accreditation of Healthcare Organizations (JCAHO), current edition; or the currently prevailing, generally recognized and accepted standard for medical record management.

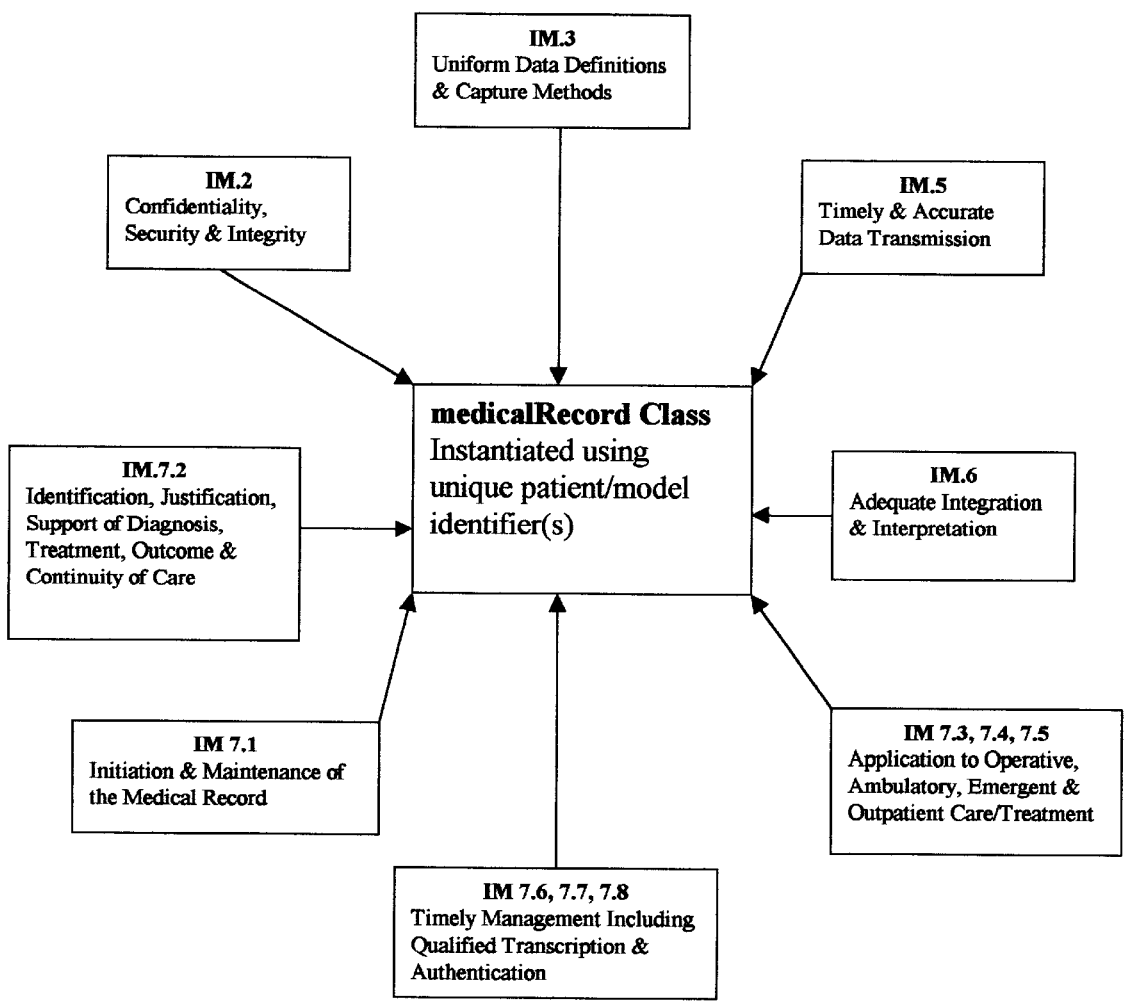

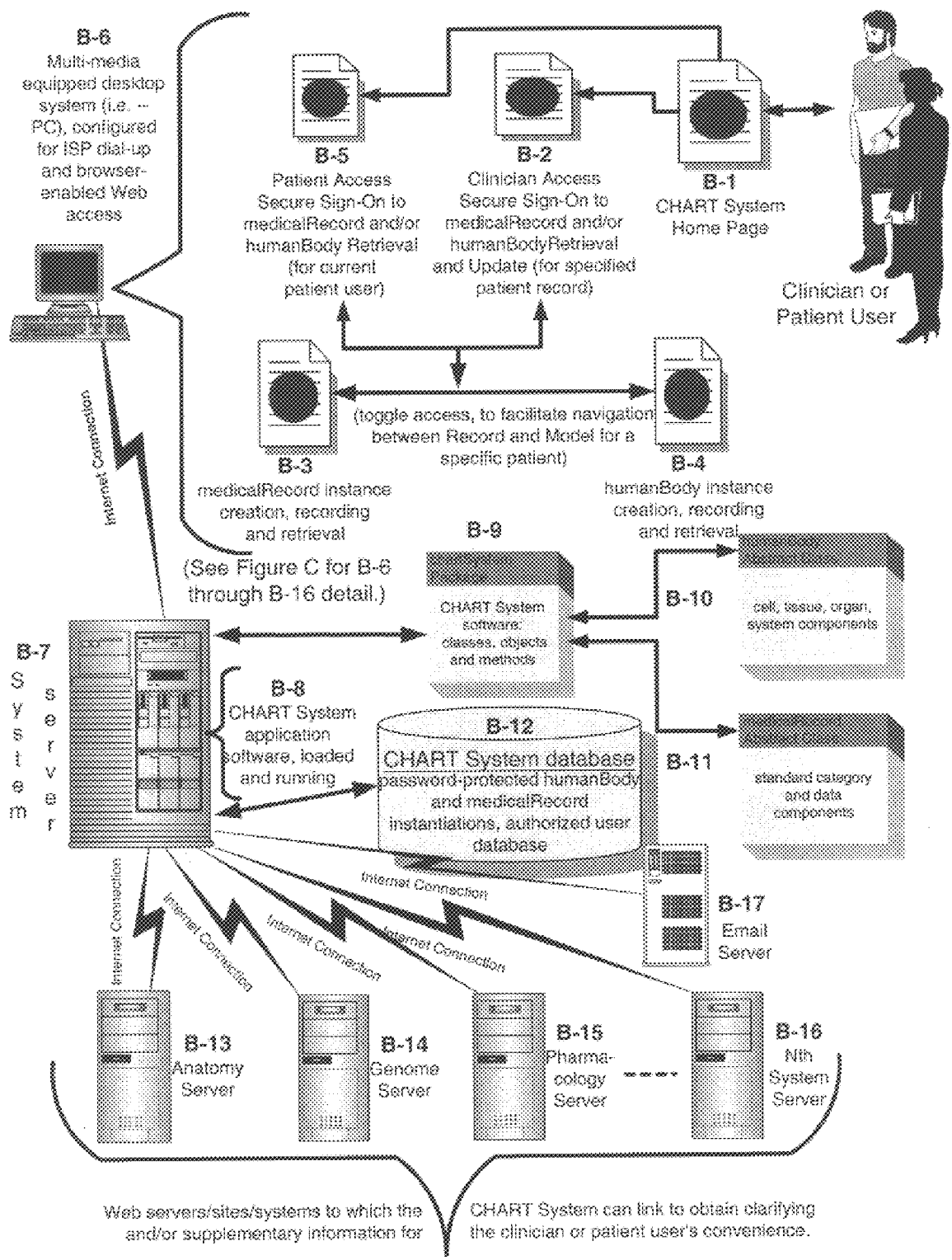

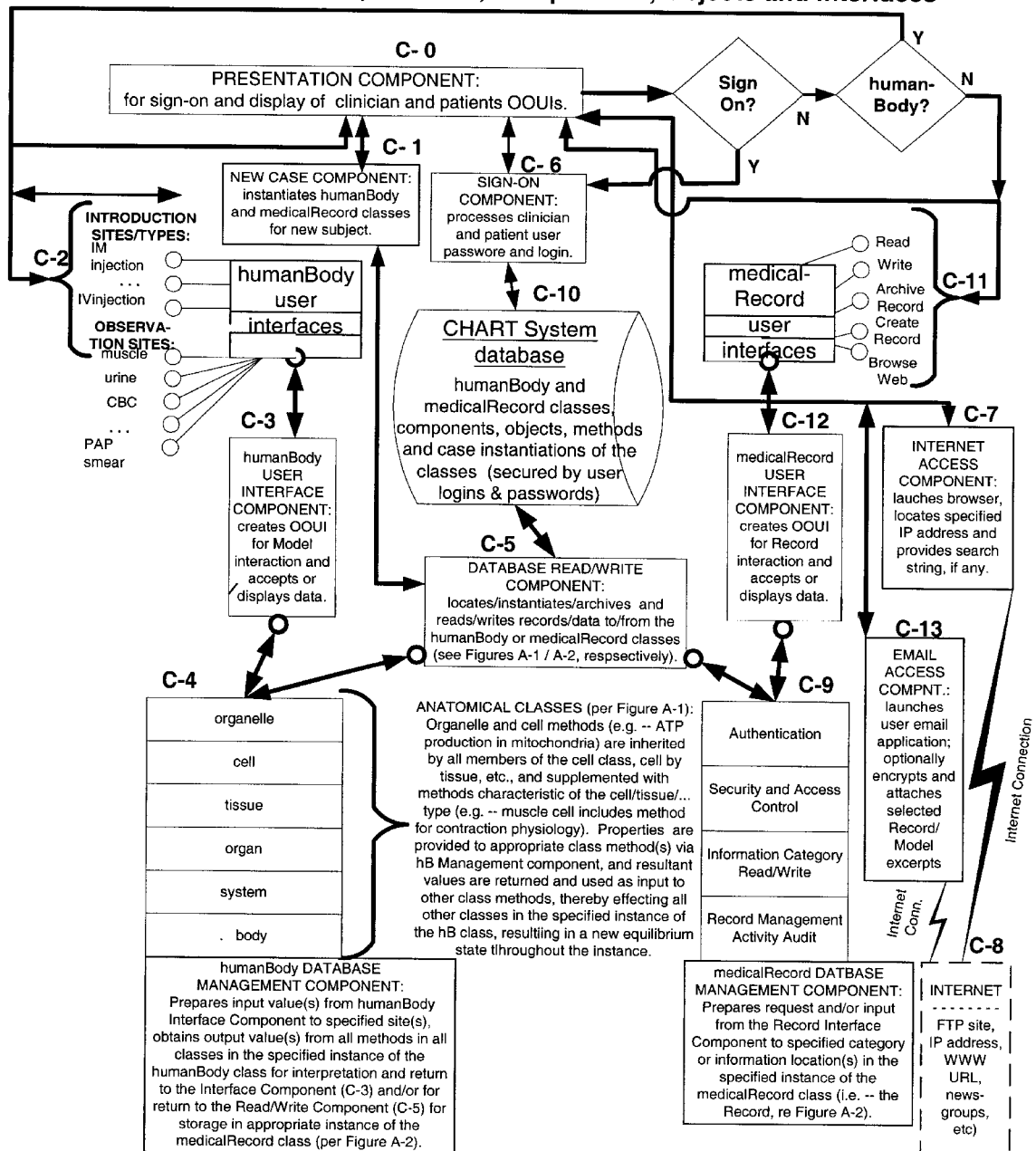
Figure C
Software Classes, Methods, Components, Objects and Interfaces

CLINICAL, HEORISTIC, ADMINSTRATIVE, RESEARCH & TEACHING (CHART) JAVA-WEB-OBJECT INFORMATION SYSTEM FOR MEDICAL RECORD MANAGEMENT PREDICATED ON HUMAN BODY ANATOMY AND PHYSIOLOGY MULTI-MEDIA MODELING

RELATED APPLICATIONS

Cross-references determined using Web site "IBM Patent Server" (patent.womplex.ibm.com) using the following boolean search text criteria and yielding the matches as noted:
a) (electronic medical record OR computerized patient record OR electronic patient record) AND (Internet OR Java OR Web OR Web-object): zero (0) matches;
b) (electronic medical record OR computerized patient record OR electronic patient record): two (2) matches with U.S. Pat. Nos. 5,609,161 and 5,452,727; and
c) (human body AND modeling AND computer): twenty-two (22) matches U.S. Pat. Nos. 5,586,224, 5,497,336, 5,652,709, 5,570,301, 5,661,668, 5,648,915, 5,625,577, 5,623,582, 5,622,170, 5,588,139, 5,249,122, 5,198,877, 3,934,226, U.S. Pat. Nos. RE34,663, 5,664,574, 5,644,232, 5,407,354, 5,315,512, 5,081,993, 5,012,522, 4,969,469 and 4,682,491.

In the opinion of the inventor, none of the references cited nor those provided by the examiner by way of example (notwithstanding their implementation of Java and other object-oriented programming technologies) include a description, embodiment or best mode requirements comparable to those of the instant application.

BACKGROUND OF THE INVENTION

1. Field of the Invention

The field of application of the invention is "human medicine", wherein there exists a continuing need to further understand and demonstrate the human body biochemical reactions and resultant physiological functions for a variety of urgent purposes, as summarized in the expansion of the CHART System name. "Chart", the term commonly used by clinical practitioners and other healthcare delivery organization staff to refer to a patient's medical record in its typical paper/hard-copy form, is used herein as an acronym (devised by the inventor of the instant application) to designate the principal areas of medical and healthcare activity—clinical, heuristic, administrative, research and teaching—on which the subject of the instant application is designed to have facilitating otherwise beneficial affects.

The field of implementation of the invention is "computer science" in general and "Web-object programming" in particular (for which the Java language is a typical but non-exclusive example of an applicable programming language). The object-oriented software attributes of "inheritance", "encapsulation" and "polymorphism" (described below) provide the information system language characteristics and processing capabilities required to implement the features and functions necessitated by the field of application.

2. Description of the Related Technology

A non-exhaustive review of the medical informatics literature and the patent file search described above reveals that a major category of the related technology, embracing a preponderance of existing computer-based representations of human physiology, are representations of physiological function and/or anatomical structure localized to a particular medical specialty, pathology and/or human body morphological component (e.g.—central nervous system structure, cardiac function, genome mapping).

A second category of computer-based representations, typically as or more specific and narrow in scope than the first, provides automated diagnostic assistance or other clinical decision support through the evolutionary application of mathematicaiboolean algorithms or, more recently, expert system or neural network technology (e.g.—the "HELP System" developed at Latter Day Saints Hospital in Salt Lake City, Utah, late in the 1960s and subsequently purchased, modified and marketed by several national hospital information system vendors).

A third category of medical computer systems is called the "electronic medical record" (EMR) or "computer-based patient record" (CPR)—the principal focus of attention during the past two decades, primarily through the efforts of the Computer-based Patient Record Institute (CPRI). Systems in this category address the issues of medical record content, utility and confidentiality in an effort to define, design and develop a computer-based "chart", the common practice name for the paper-based medical record as defined above. The principal purpose of the computer-based chart is to make patient-specific information available to clinicians when and where it is needed in order to facilitate more efficient, effective and (therefore) economical pathology diagnosis and treatment, and ongoing patient care including clinical monitoring.

SUMMARY OF THE INVENTION

The CHART System (herein after referred to as "the System"), which is the subject of the instant application, features secure but generally available access via any Internet-based World Wide Web (a/k/a "the Web") connection to a real-time interactive physiological model of the human body and associated computer-based patient record to provide capabilities of four types.

1) The System includes features and functions for the establishment and manipulation of the human physiology model for both real (e.g.—patient-specific, at selected points in time) and/or hypothetical (e.g.—research or prospective/what-if modeling) total human systems.

2) The System includes features and functions for the establishment and maintenance of a medical chart used to described the physiological information determined and demonstrated by the companion instance of the human body mode.

3) The System leverages the extensive and varied array of Internet-based multi-media information by invoking, on user demand or automatically, those information resources most appropriate to supplement the model data; these resources might include multi-media anatomical information (e.g.—gross anatomy structure and function depiction) or diagnostic/therapeutic descriptive information (e.g.—electrocardiography (EKG) and electroencephalography (EEG) tracings), or whatever may be currently available at authoritative Internet sites.

4) The System provides an integrated email facility for communication of model and/or medical record information, at the discretion of the user, to any holder of a currently active email account; this facility enables the user to attach designated information to an email message using the currently acceptable degree of data encryption (e.g.—at the date of the instant application submission, 124-bit "PSGP" encryption).

A case-specific copy of the human body physiology model is a software construct that includes the functionality (i.e.—the methods or behaviors) of the general model and the manifestations (i.e.—the properties or states) of a specific and stand-alone "case", examples of the latter of which include:

1) an actual patient's baseline/normal condition,
2) an actual patient's current/pathological condition,
3) an actual patient's hypothetical or "what-if" condition following contemplated administration of a new medication, change in diet and/or other introduction of a foreign chemical substance (as in poison trauma),
4) an experimental protocol-specific case, pre- or post-treatment, or
5) a clinical trial subject condition, pre- or post-protocol administration.

In response to appropriate application of these tools to record biochemical, nutrient, toxin or other "foreign substance" input to the System model at one or more sites of introduction/absorption, the System determines and then demonstrates in real time the resulting effects on the instantiated model at any/all other anatomic sites for which user interfaces are provided (planned to include all clinically useful or significant sites of physical examination, test application and specima collection.

In a practical application, the System can be applied by a licensed clinician to an instantiation of any appropriate case (as defined above) at the genome, organelle, cell, tissue, organ, system and/or whole body level as an aide to health maintenance, diagnosis and treatment. To enhance the benefit of the model output, multi-media data displays consistent with the subject data types (e.g.—audio for heart sounds, graphics for EEG, etc.) are made available on request or automatically via "links" to commercial, not-for-profit, public agency or other Internet/Web sites and/or information sources resident on the System's server platform, the programmed logical pathways to which are specified and easily modifiable in the System. In addition, the System architecture provides interfaces and links to other facilities for information management support of clinical procedures, ancillary to the patient care process (e.g.— pharmacology compounding and dose determination, (ab) normal growth and development assessment, genetic predisposition determination, etc.), to the extent that this information is available on other authoritative Internet sites for which electronic "paths" can be specified.

Notwithstanding their broad scope, ready accessibility and rich content, the CHART System features/functions are intended to serve only as medical education and clinical decision support aides to licensed clinician users in their diagnostic, therapeutic and patient care activities. The CHART System purpose is neither to preempt nor to minimize the professional participation and responsibility of the licensed clinician user in the diagnostic, therapeutic and care processes; but, rather, to maximize the economy, efficiency and effectiveness of these processes (and, consequently, the clinician's availability of time for other medical/clinical purposes). This maximization is achieved principally as a result of the complete, accurate and timely management of anatomical and physiological information by the System with minimal effort by the clinician.

In addition, the CHART System can provide patients with secure, read-only Web access to their personal medical information; and both clinicians and patients can authorize access by anyone anywhere to System features, functions and information, up to and including the extent of access privileges held by the authorizing clinician or patient. However, although accessibility to all CHART System features/functions is potentially as ubiquitous as the Internet; nevertheless, System access can be limited even at the individual user level, using generally available information technology and generally accepted standards and practices for its application, consistent with prevailing laws and regulations.

The principal nuance of the CHART System lies in its comprehensive implementation of the direct analogy between the characteristics of human anatomy and physiology and those of object-oriented programming (OOP): the complex biochemical equilibrium of each and every morphological element of the body and their interactions with all others are emulated by implementing the OOP concepts of "encapsulation", "inheritance" and "polymorphism". For example (using OOP terminology, enclosed by quotation marks " ", in the following example), a gastrointestinal epithelial lining cell and a renal epithelial cell (both derivatives of the stem cell and then of the undifferentiated epithelial cell in human anatomic ontology) each are represented in the model as separate "object sub-classes" of the epithelial cell "class" that "inherit" (include) the "methods" and "properties" (the behaviors, or physiological characteristics; and states, or typical biochemical concentrations of reactants and catalysts/enzymes) of the stem cell and epithelial cell "classes". In addition, each is programmed to include other "methods" and "properties" that are physiologically unique to each and are hidden from biochemical transfers (emulated by "overloaded messaging") and reactions with other "class methods" (emulated by biochemical equilibrium equations) through "encapsulation".

Continuing the example, a change in the "properties" (state values) of the gastrointestinal epithelial cell "class" (induced, for instance, by the input of data via the "object-oriented user interface" representing oral introduction a/k/a ingestion of a particular oral medication) is emulated by recalculation of the biochemical equation "class methods" in the "instantiation" of the human body model "abstract class" substituting the new data in the biochemical equations representing the "class" "methods" for those "classes" emulating the oral, esophageal and gastric (i.e.—mouth, throat and stomach) epithelial tissue, and a modified biochemical equilibrium is reached as emulated by changes in state values or "properties" for each of the directly effected "class" "methods". The new values are retained and/or passed selectively through "interfaces" and "message overloading", whereby a single message is sent to all other "methods" for receipt and processing conditional on the "methods" and "properties" included in each receiving "class" (emulating the metabolism and transport of metabolites throughout the human body, as further detailed below).

Concluding the example, this implementation of OOP operations emulates the function of the typical semi-permeable cell membrane and incorporated physiological chemical transfer mechanisms such as the $Na^+/K^+$ pump, for cross-membrane transfer of sodium and potassium ions and intra-corporeal fluid transfer vehicles such as interstitial fluid, lymph and blood. The output variables thus are incorporated by the "exposed interfaces" of other "classes" representing any/all other human body anatomical structures at all morphological levels—intracellular, cell, tissue, organ and system. For instance, variables selectively received and incorporated by the renal epithelial cell "class", are processed as input to particular "methods" included in that "class". New biochemical equilibria are calculated for that "class" which, in turn, may effect the equilibrium states of other classes through transmission and receipt of selected "property" values via "messaging overloading" to be processed by the "methods" included in other "classes". A manifold, ubiquitous occurrence of this OOP processing scenario throughout the "instantiation" of the human body model "abstract class" yields a modified state of equilibrium for the entire "instantiated" model, following which the model can be inspected via various "object-oriented user interfaces" designed to represent typical sites of physical examination or specimen collection (e.g.—urine, spinal fluid, oral epithelial lining or "mouth swab", cervical epithelial lining or "Pap smear", blood or "complete blood count (CBC)", etc.).

The features/functions of the foregoing example of the System human body model conform to the behaviors/methods and states/properties of human biochemistry and physiology, to the extent that they are identified and described in the current authoritative medical literature and implemented in the System. The System is programmed using a robust, interoperable (i.e.—capable of running on any computing platform) and generally accepted OOP language with development and runtime environments (e.g.—Java, including a language compiler and the Java Virtual Machine). The OOP language defines the "chartSystem package", including the "humanBody" and "medicalRecord" abstract classes, using "components", "objects" and "interfaces" to model the biochemical physiological workings of the body at all anatomic levels—intracellular to whole body.

The CHART System incorporates graphical user interfaces, object-oriented user interfaces and object-oriented programming best practices, implemented in compliance with the Distributed Component and Object Model, the Common Object Request Broker Architecture and other current and applicable industry standards for Web-object system design and development. The System software operates on dedicated Web-based "server" systems and any Internet-connected "client" system (typically a personal computer (PC) configured with "Web browser" software). The clinician or patient user accesses the System's human body model, medical record and other facilities via any client system using the intuitive, easy-to-use, flexible and robust interactive information management user interfaces that are included to define, explore or update an "instantiated" model.

BRIEF DESCRIPTION OF THE DRAWINGS

The inventor has included four figures—labeled "A1", "A2", "B" and "C"—as an integral part of the instant application, which are described as follows, using object-oriented programming (OOP) terms (enclosed with quotation marks, " ") and including technical terminology common to the practice of Web-object programming:

A) chartSystem Package—hierarchical diagrams, including:
1) humanBody Abstract Class Inheritance Hierarchy, a schematic of the "class" definition and "messaging" design approach for the System human physiology "object classes" (FIG. A1);
2) medicalRecord Abstract Class Inheritance Hierarchy, a schematic of the "class" definition and "messaging" design approach for the System medical record object classes (FIG. A2);

B) Hardware and Software Element Configuration—a schematic showing the relationship and interaction of the System hardware and software elements, pertinent to the operation of both the physiology model and the medical record; and C) Software Classes, Methods, Components and Interfaces—a schematic showing the relationship and interaction of software "classes", "components", "objects", "interfaces" and "files", pertinent to the operation of both the physiology and the medical record models.

DETAILED DESCRIPTION OF THE PREFERRED EMBODIMENT

N.B.—Notations in brackets, [ ], refer to specific items in FIG. A, chartSystem Package Hierarchies, including FIG. A1, humanBody Abstract Class, and FIG. A2, medicalRecord Abstract Class; FIG. B, Hardware and Software Element Configuration; and FIG. C, Software Classes, Methods, Components and Interfaces, all of which are included as an integral part of the instant application. Any personal computer (PC) screen display generated by Web site software is herein after referred to in Web terminology as a "page".

1. The clinician or patient user accesses and manipulates the System to begin a session of use (i.e.—a period of user-System interaction delimited by sign-on and sign-off operations) by operating an appropriately configured and connected PC [B-6] to logon to the PC, to connect to the Internet, to navigate to the System Web site "home page" [B-1] (i.e.—the first/beginning screen display), to identify his/her status as "patient" or "clinician", and to obtain the appropriate sign-on page [B-2 or B-5].

2. The System software [B-9, C-10] running on the system server [B-7] supports this interaction in Step 1, above, by initiating access to and operation of the required hardware [B-7] and software [B-9, C-10] and database [B-12/C-10].

3. The user operates the System by observing client system PC [B-6] monitor displays of System Web site pages and by responding to each page display, a/k/a object-oriented user interface (OOUI) [B-1, B-2, B-3, B-4, B-5], through PC-based keyboard- and mouse-enabled entry/input of data/responses to the System pages controlled by System presentation component [C-0].

4. To initiate a System session (i.e.—a use of the System, extending from user sign-on to user sign-off for a the same user) the user-System interaction occurs as follows:

4.1. the user navigates to the appropriate secure sign-on page [B-5 or B-2] according to user type—patient or clinician;

4.2. the user inputs login and password [C-0], as previously provided following regulations yet to be defined (which definition is pertinent to the commercial implementation of the invention and the maintenance of patient information privacy, but which is irrelevant to the instant application);

4.3. the System processes user sign-on data together with previously input and filed user identification data [C-0, C-6, C-10 in part] to authenticate the user and to determine authorized uses of the System;

5. Pending the outcome of user authentication and authorization, the System (dis)allows user access and user-System interaction, and the System locates and locks the user-specified case class instantiations as follows:

5.1. if the specified instantiations do not exist (i.e.—the case is new, and no class instantiations exist), then:

5.1.1 the System instantiates the human physiology model, a/k/a "the humanBody" class [A-1, in toto], and the electronic medical record, a/k/a "medicalRecord" class [A-2 in toto] via the presentation component [C-0], the new case component [C-1] and the database read/write component [C-5], 5.1.2. the System requests from the user the minimum required property/state values for a valid instantiation (e.g.—for the medicalRecord, patient identification and demographic data; for the humanBody, patient anatomical and physiological baseline data);

5.2. if the specified case (i.e.—combination of humanBody and medicalRecord instantiations) does exist, then the System opens and locks those instantiations.

6. The System establishes software pathways to/from:

6.1. the specified instantiations of the humanBody and medicalRecord classes via the presentation component [C-0], the humanBody and medicalRecord user interfaces [C-2, C-11], the humanBody and medicalRecord user interface components [C-3, C-12], the humanBody and medicalRecord database management components [C-4, C-9], the database read/write component [C-5] and the humanBody class [B-10] and medicalRecord class [B-11] in the CHART System database [B-12/C-10];

6.2. specific Internet/Web sites, as/if directed by a System component or requested by the user, to obtain supplemental information about the subject humanBody instantiation behaviors or states via the presentation object [C-0] (if requested by the user) running on the client system [B-6] and the Internet access object [C-7] running on the system server [B-7] through the Internet [C-8] to the selected Internet/Web site(s) [B-13, B-14, B-15, B-16]; and/or 6.3. email server [B-17], as/if requested by the user, via the presentation object [C-0] running on the client system [B-6], the email access object implementing encrypted attachments [C-13] running on the system server [B-7] and the user's email software client running on the user's client system [B-6] through the Internet [C-8] to the user's email service provider's server [B-17] and through the Internet to any email addressee(s) selected by the user;

6.4. the System responds to user entry/input with a variety of OOP features and functions limited by user authorization and and/or the purpose/target of the current user session—humanBody or medicalRecord.

7. To interact with the specified humanBody and medicalRecord class instantiations, the user:

7.71 toggles between the humanBody and medicalRecord instantiations, as needed, via the System Web site pages [B-4, B-3] controlled by the presentation component [C-0], the user interfaces [C-2, C-11], the user interface components [C-3, C-11], the database management components [C-4, C-9], the database read/write component [C-5] and the database [B-12/C-10];

7.2. navigates within the specified instance of the medicalRecord [B-11, B-12] using the System software [B-9, B-12, C-10], which implements the medicalRecord abstract class of objects [A-2, B-11] that loads and executes [B-8] on the System server [B-7] and reads, writes, modifies and/or archives the selected instance of the medicalRecord via the presentation component [C-1], the medicalRecord interfaces [C-11], medicalRecord user interface component [C-12], the medicalRecord database management object [C-9], the database read/write component [C-5] and the database [B-12/C-10];

7.3. navigates within the specified instance of the humanBody [B-10, B-12], using the System software [B-9, B-12, C-10], which implements the humanBody abstract class of objects [A1-1, A1-2, A1-3, A1-4, A1-5, B-10] that loads and executes on [B-8] on the System server [B-7] and reads, writes, modifies and/or archives the selected instance of the humanBody via the presentation component [C-1], the humanBody interfaces [C-2], humanBody user interface component [C-3]; the humanBody database management object [C-4], the database read/write component [C-5] and the database [B-12/C-10];

7.4. uses the System as appropriate to determine, using the humanBody class [B-10, C-4]; to demonstrate, using the humanBody class [B-10, C-0, C-2, C-3, C-4, C-5, C-10] and the Internet/Web site access components [B-7, B-13, B-14, B-15, B-16, C-0, C-11, C-7, C-8]; to document, using the medicalRecord class [B-11, C-0, C-11, C-12, C-9, C-5, C-10]; and to distribute, using the email access facility [B-17, C-0, C-13, C-8] data and information about the physiological state of the case represented by the selected humanBody and medicalRecord class instantiation, examples of which are detailed in step 8, below.

8. To use the System for its intended purpose, the user provides records data input to a selected instantiation of the humanBody class and its associated medicalRecord class, the System operates on the input data, and the user observes the output data and interprets and records it as follows:

8.1. the user simulates introduction of a substance (e.g.—nutrient, pharmacological agent, toxin) by selecting an object-oriented user interface (OOUI) [A1-6, B-4, C-0, C-2, C-3] specific to the selected route of administration or introduction (e.g.—intravenous, oral) and recording the required input data in the field(s) of the selected OOUI, which describe the substance composition, concentration, quantity and frequency of administration (e.g.—1 liter 5 percent saline solution stat, 2 tablets of 300 milligrams calcium bid), 8.2. the System receives and the input data and distributes the data by extensive use of "overloaded messages" among the several components and objects that make up the humanBody class [B-7, B-8, B-9, B-10, C-3, C-4, C-5, C-10], thus emulating the physiological conveyance of the ingested or otherwise introduced substance represented by the input data, via blood, lymph, interstitial fluid, etc. to the anatomical structures and morphological levels [A1-1, A1-2, A1-3, A1-4, A1-5], 8.3. the System executes the biochemical equilibrium equation methods included in those objects and components programmed to receive the input data messages which contain the property/state values for those methods, thus emulating:

8.3.1. the biochemical physiology occurring within organelles at the intracellular level [A1-1, A1-2] and, consequently 8.3.2. occuring between cells at the intercellular, tissue, organ and system levels of the human body anatomy [A1-1, A1-2, A1-3, A1-4, A1-5], resulting in 8.3.3. a complete recalculation of all the included equations and reevaluation of all property/state values for all effected physiological methods/behaviors;

8.4. the user observes and investigates the resultant effect(s) of substance introduction on the behaviors and states of the humanBody instance by:

8.4.1. selecting the OOUI [C-2] specific to the anatomical site or specimen of interest (e.g.—peripheral blood, long-bone marrow, urine) [A1-7] and the specific biochemical or physiological state(s) to be displayed [C-2, C-3, C-4, C-5, C-10];

8.4.2. observing, optionally, correlate anatomic manifestations of the site behavior and state data and/or studies medical implications of behavior and state data using multi-media information maintained at other Internet/Web sites (e.g.—MicroMedex, Harrison's On-line, ADAM, Ovid, DXplain) that are accessed by user input of appropriate universal resource locator(s) (URLs) or by browsing to site(s) [B-13, B-14, B-15, B-16, C-7] for which URL(s) are programmed in and automatically activated by the System, according to the selected output OOUI [C-2, C-3];

8.5. the user specifies, optionally, instantiation of the input, processing and output to create a permanent record of the current use of the System, in response to which the System:

8.5.1. instantiates the specified instance of the humanBody class [B-4, B-8, B-9, B-10, B-11, B-12, C-0, C-1, C-5, C-10] recording the current behaviors and states of the specified case, 8.5.2. records selected or previously specified data reflecting the new instantiation of the humanBody class in the medicalRecord instantiation [A2] for the specified case [B-3, B-8, B-9, B-11, B-12] by identifying anatomic sites [C-0, C-2, C-3] for which the associated method/behavior and property/state data [C-4, C-5, C-10] are automatically written to the appropriate locations in the single instantiation of the medicalRecord related to the specified case [C-9, C-5, C-10] consistent with current law and regulation for medical record update and maintenance (e.g.—including "authentication" information, preserving previously current information in read-only mode).

8.6. the user sends email [B-17], with/without excerpts from the user-specific instance of the humanBody and/or medicalRecord as encrypted attachment(s) [C-0, C-3, C-12, C-13], to communicate the selected information to any email addressee deemed appropriate by the user (patient or clinician) for medical consultation, for third-party payor approval or reimbursement, or for social/lay communication with any specified email address(es).

The inventor claims:

1. A Web-object computer system hardware and software architecture for real-time human body physiology modeling and medical record-keeping named the Clinical, Heuristic, Administrative, Research & Teaching (CHART) System, which is an application of the following industry-standard information technology hardware components, object-oriented programming (OOP) scripts, OOP class and interface definitions and object-oriented user interfaces (OOUIs), the broad, physiologically comprehensive scope of which and real-time interoperability throughout are unique to the instant application:

a) a client system (i.e.—any personal computer (PC) configured for multi-media support and Internet access) to be used for:
  i) access to the System Web site,
  ii) input of data describing site-/route-specific introduction/administration of foreign substances,
  iii) multi-media display of information describing the biochemical, physiological and anatomical state(s) of the human body at specific site(s), and
  iv) access to related Internet sites as/if required;

b) a Web server system array (i.e.—two or more dynamically allocated Internet-accessible computer systems, the configuration of which is typified by that provided maintained at an Internet service provider (ISP) "server farm"), including:

i) a hardware and software platform for operation of the CHART System Web site,
  ii) management on intercommunicating random access data storage device(s) (e.g.—a "RAID") of the CHART System software (i.e.—the chartSystem Package of object classes, the OOP language virtual machine, integrated development environment (IDE) with which the CHART System is maintained and modified, and instantiations of the humanBody and the medicalRecord abstract classes as created and maintained by CHART System users),
  iii) management of multiple, concurrent CHART System user activities including secure sign-on, and download and operation of the CHART System OOUIs to the user-operated client system(s),
  iv) operation of the CHART System software and/or control of the distributed operation of CHART System software on other Internet-accessible servers:
    a) to process input to the selected instantiations of the humanBody and/or medicalRecord classes,
    b) to display the biochemical and physiological behaviors and states of the user-selected site(s) of the target class instantiation(s),
    c) to update selected instantiation(s) of the humanBody and medicalRecord classes, per user direction, and
    d) to launch browser software for automatic or user-directed access to selected Internet sites not a part of the instant application but useful for further anatomic and/or physiological demonstration of CHART System class instance output.

2. An object-oriented programming (OOP) "package" of classes with included methods and properties—implemented using components, objects, messages, object interfaces, scripts and object-oriented user interfaces (OOUIs) including third-party software "controls"—all of which are programmed and executed per the architecture of claim 1 of the instant application in a manner that is unique by virtue of its comprehensive scope and real-time interoperability, as follows:

a) clinically intuitive OOUIs for:
  i) input of foreign substance introduction/administration data including drop-down windows for:
    a) site/route (e.g.—intramuscular),
    b) substance (e.g.—insulin),
    c) form (e.g.—liquid/injectable),
    d) concentration (e.g.—x milligrams per milliliter),
    e) quantity (e.g.—y milliliters),
    f) frequency (e.g.—bid/twice daily);
  ii) output of site-/class-specific status/state information in biochemical terms with multi-media enhancement, implemented by coded linns to other Internet/Web sites that are professionally maintained and publicly accessible(e.g.—Digitalis active ingredient levels in heart muscle, linked to audio-visual depiction of heart function under specified biochemical conditions from the ADAM Web site);
  iii) management of patient-/case-specific instantiations of the humanBody abstract class and the medicalRecord abstract class including:
    a) creation of a new instance, requiring user input of data describing the new subject in medical history and physical examination terms (i.e.— demographics, sex, age, weight, health status and other parameters having empirical significance for the execution of humanBody modeling capabilities such as metabolic equilibrium, pharmacological calculation, hormone balance, etc.), b) modification of an existing instantiation or, optionally, creation of an additional instantiation of the humanBody class with changed properties/states for the same case subject as a means for retaining a model of the current/atypical/diseased/remarkable condition of the same subject, c) automatic update of medicalRecord class instance with output from the related humanBody instance(s) at the direction of but without manual data entry by the user, d) archiving of humanBody class and medicalRecord class instance data to random- or limited-access media (e.g.—hard disk, magnetic tape, CD-ROM, etc.);

b) OOP (sub-/super-)classes, components and component interfaces that:

i) describe the human body at each and every anatomic level—sub-nuclear/organelle/genome, cell, tissue, organ, system, body—including for each class:

a) biochemical states/properties in terms appropriate to the anatomical-physiological target (e.g.—concentration of sodium (NA+) and potassium (K+) ions within and immediately without a neuron, and the local concentration of acetylcholine (ACH)), b) physiological behaviors/methods that occur in the target anatomical structure (e.g.—the adenylate cylcase-/cAMP-generating system in neurons), c) physiology transport mechanisms pertinent to the anatomical/physiological target (e.g.—the ACH channel mechanism for controlling the passage of N+ and K+ ions to/from the immediately proximal interstitial fluid (ISF), a/k/a the "sodium-potassium pump");

ii) utilize OOP features/functions/tools in a manner that emulates the differential anatomical structures and physiological functions, including:

a) "encapsulation", to hide the methods/behaviors of a structure in the confines of that structure, b) "inheritance", to include the methods/behaviors and properties/states of structures defined at higher levels of the humanBody abstract class hierarchy, which represent the simpler and more physiologically fundamental and pervasive structures and functions occur at the higher hierarchical levels, c) "polymorphism", to obtain a wide variation among fundamentally equal structures by the combination of:

(1) encapsulation for data hiding, (2) addition of specialized methods/behaviors and properties/states at various morphological levels to implement level-specific uniqueness, and (3) message "overloading" to trigger class-specific differential method execution and property transformation through common method naming;

iii) apply the user input state values to the selected OOUI methods and properties of the specified instantiation of the humanBody abstract class, implementing all messages and targeted methods immediately and concurrently to:

a) determine the new equilibrium state of the humanBody instance at large with acceptable response time, and b) demonstrate a user-specified subset thereof on demand:

(1) via the appropriate OOUI, and/or (2) employing other servers located in the ISP server farm or remotely, via the Internet, as/if requested by the user or directed by the System design.

* * * * *

UNITED STATES PATENT AND TRADEMARK OFFICE
CERTIFICATE OF CORRECTION

PATENT NO. : 6,272,468 B1
DATED : August 7, 2001
INVENTOR(S) : John Peter Melrose It is certified that error appears in the above-identified patent and that said Letters Patent is hereby corrected as shown below:

Title page, Item [54] and Column 1, line 1,
Change "HEORISTIC" to -- HEURISTIC --.
Item [76], change "108 Lee Dr., Annapolis, MD (US) 21403" to -- 6901 73RD Ave. N., Brooklyn Park, MN (US) 55428".

Column 1,
Line 1, change "HEORISTIC" to -- HEURISTIC --.

Column 2,
Line 7, change "mathematicaiboolean" to -- mathematical/Boolean --.
Line 64, change " "PSGP" " with -- "PGP" --.

Column 3,
Line 24, change "collection." to -- collection). --.

Column 4,
Line 65, change "turu" to -- turn --.

Column 9,
Line 3, change "studies" to -- studying --.

Column 10,
Lines 1-2, change "provided maintained" to -- provided and maintained --.
Lines 6-7, change "random access data storage device(s)" to -- redundantarray of inexpensive disks --.
Line 46, change "administration data" to -- administration of data --.
Line 53, change "bid/twice daily)" to -- bid (I.E.-twice daily)) --.
Line 56, change "linns" to -- links --.

UNITED STATES PATENT AND TRADEMARK OFFICE
CERTIFICATE OF CORRECTION

PATENT NO. : 6,272,468 B1
DATED : August 7, 2001
INVENTOR(S) : John Peter Melrose It is certified that error appears in the above-identified patent and that said Letters Patent is hereby corrected as shown below:

Column 11,
Line 24, change "body" to -- body (Figure A1) --.

Signed and Sealed this

Twenty-fifth Day of February, 2003

JAMES E. ROGAN
*Director of the United States Patent and Trademark Office*